United States Patent [19]
Bender et al.

[11] 3,980,788
[45] Sept. 14, 1976

[54] PHARMACEUTICAL COMPOSITIONS AND METHODS OF INHIBITING GASTRIC ACID SECRETION

[75] Inventors: Paul E. Bender, Willingboro, N.J.; Bernard Loev, Broomall, Pa.

[73] Assignee: SmithKline Corporation, Philadelphia, Pa.

[22] Filed: Sept. 15, 1975

[21] Appl. No.: 613,689

[52] U.S. Cl. .......................... 424/267; 260/293.58; 260/326.5 CA; 424/274
[51] Int. Cl.$^2$ ....................................... C07D 405/04
[58] Field of Search ............... 260/293.58; 424/267, 424/274

[56] References Cited
UNITED STATES PATENTS
3,558,779   1/1971   Adams et al. ..................... 424/283

OTHER PUBLICATIONS
Witiak et al., J. Med. Chem. 17, 690–696 (1974).

*Primary Examiner*—G. Thomas Todd
*Attorney, Agent, or Firm*—Joan S. Keps; Richard D. Foggio; William H. Edgerton

[57] ABSTRACT

Pharmaceutical compositions and methods of inhibiting gastric acid secretion by administering 1-(9-xanthenyl) amino-substituted-piperidines and pyrrolidines and new 1-(9-xanthenyl) amino-piperidine compounds.

20 Claims, No Drawings

PHARMACEUTICAL COMPOSITIONS AND METHODS OF INHIBITING GASTRIC ACID SECRETION

This invention relates to new pharmaceutical compositions and methods of inhibiting gastric acid secretion by administering 1-(9-xanthenyl) piperidines and pyrrolidines having an amino substituent on the piperidine or pyrrolidine ring. In addition, this invention relates to new 1-(9-xanthenyl) amino-substituted-piperidine compounds.

The pharmaceutical compositions of this invention having gastric acid secretion inhibitory activity, in dosage unit form, comprise a pharmaceutical carrier and a xanthenyl amino-piperidine or pyrrolidine compound of the formula:

FORMULA I

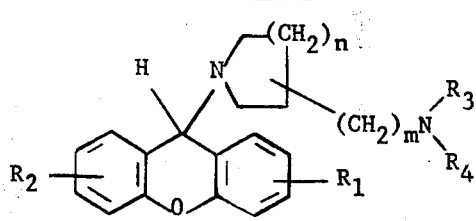

in which:
$n$ is 1 or 2;
$m$ is 0, 1, 2 or 3;
$R_1$ is hydrogen, halogen, hydroxy, lower alkyl or lower alkoxy;
$R_2$ is hydrogen, halogen, lower alkyl or lower alkoxy;
$R_3$ is lower alkyl and
$R_4$ is hydrogen, lower alkyl or lower alkanoyl or a pharmaceutically acceptable acid addition salt thereof, with the proviso that when $m$ is 0 the amino group is not attached at the 2-position.

Preferably, in Formula I, $R_1$ and $R_2$, being the same or different, are hydrogen, chloro, methyl or methoxy. In addition, most preferably, $n$ is 2, $R_1$ and $R_2$ are hydrogen and $R_4$ is lower alkyl.

An advantageous pharmaceutical composition of this invention comprises, in dosage unit form, a pharmaceutical carrier and 1-(9-xanthenyl)-3-dimethylaminopiperidine.

When the amino group is attached at the 2 or 3 position of the piperidine ring or when the ring is pyrrolidine or when $R_1$ and $R_2$ are different, compounds of Formula I may exist as the d or l isomers. These isomers as well as the dl mixtures thereof are included within the active ingredients of the pharmaceutical compositions and methods of this invention.

The new 1-(9-xanthenyl) amino-substituted-piperidines of this invention are represented by the following formula:

FORMULA II

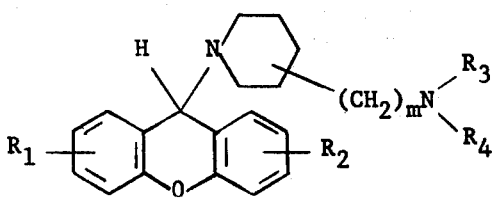

in which:
$m$ is 0, 1, 2 or 3;
$R_1$ is hydrogen, halogen, hydroxy, lower alkyl or lower alkoxy;
$R_2$ is hydrogen, halogen, lower alkyl or lower alkoxy;
$R_3$ is lower alkyl and
$R_4$ is hydrogen, lower alkyl or lower alkanoyl or a pharmaceutically acceptable acid addition salt thereof, with the proviso that when $m$ is 0, the amino group is not attached at the 2-position.

In preferred compounds of Formula II, $R_1$ and $R_2$, being the same or different, are hydrogen, chloro, methyl or methoxy. Most preferably, $R_1$ and $R_2$ are hydrogen and $R_4$ is lower alkyl.

A particularly preferred compound of Formula II is 1-(9-xanthenyl)-3-dimethylaminopiperidine.

The gastric acid secretion inhibitory activity of the compounds of Formulas I and II is demonstrated by administration to pylorus ligated rats at doses of about 10 to 50 mg./kg. orally. In addition, this activity is shown by intraduodenal administration to pylorus ligated rats of 1.25–50 mg./kg. of 1-(9-xanthenyl)-3-dimethylaminopiperidine, 2.5–20 mg./kg. of 1-(9-xanthenyl)-4-dimethylaminopiperidine and 5–20 mg./kg. of 1-(9-xanthenyl)-2-(2-dimethylaminoethyl)piperidine. Also, gastric acid secretion inhibitory activity of the compounds of Formulas I and II is demonstrated by administration to chronic gastric fistula monkeys at doses of about 7.5 to 15 mg./kg. by intragastric administration. In these procedures, compounds which produce an increase in gastric pH or a decrease in volume of gastric juice or both are considered active.

The compounds of this invention show antiulcer activity, for example in the restraint-stress method in which on oral administration to rats at doses of about 10 to 40 mg./kg. these compounds inhibit the development of experimental ulcers.

These compounds, which inhibit gastric acid secretion, are useful in treating gastric and duodenal ulcer disease and other conditions involving gastric acid hypersecretion.

The compounds of Formula I (including also the compounds of Formula II) are prepared by the following procedures.

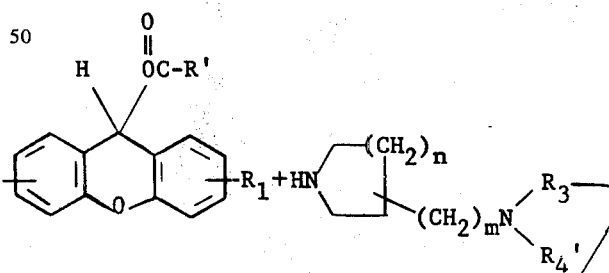

FORMULA III        FORMULA IV

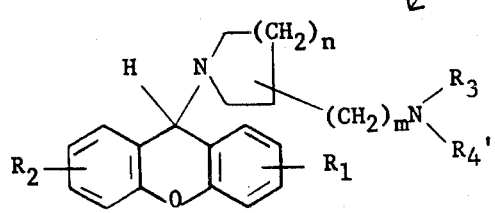

The terms $R_1$–$R_3$, $m$ and $n$ are as defined above, $R_4'$ is lower alkyl or a protecting group such as carboalkoxy or benzoyl and $R'$ is lower alkyl, preferably methyl.

According to the above procedure, a 9-xanthenyl alkanoate of Formula III is reacted with a N,N-disubstituted aminopiperidine or pyrrolidine. The reaction is preferably carried out in an inert solvent such as benzene or toluene, at elevated temperature, conveniently at reflux temperature.

The compounds of Formula I in which $R_4$ is hydrogen are prepared by treating the corresponding compounds in which $R_4$ is lower alkoxycarbonyl, such as ethoxycarbonyl, or a benzoyl group with base such as potassium hydroxide in aqueous ethanol.

The compounds of Formula I in which $R_4$ is lower alkanoyl are prepared by reacting the compounds in which $R_4$ is hydrogen with a lower alkanoylating agent such as a lower alkanoyl anhydride or halide.

The 9-xanthenyl alkanoate starting materials are either known to the art or are prepared from xanthydrols by reacting with a lower alkyl isocyanate to give a 9-lower alkylcarbamoyloxyxanthene and reacting that intermediate with a lower alkanoic acid.

The xanthydrols are either known to the art or are prepared by the following procedure. A 2-halobenzoic acid is reacted with a phenol preferably in the presence of a base such as potassium carbonate and in the presence of cuprous iodide and copper bronze. The resulting 2-phenoxy-benzoic acid is cyclized by treating with acid for example polyphosphoric acid. The resulting xanthone is reduced, for example using sodium amalgam in ethanol, to give the xanthydrol.

The N,N-substituted aminopiperidine and pyrrolidine starting materials (compounds of Formula IV in which $M$ is 0) are either known to the art or are prepared by reductive amination of N-benzylpiperidones or pyrrolidinones to give a lower alkylamino-N-benzylpiperidine or pyrrolidine, then N-alkylating by standard procedures to give the di-lower alkylamino-N-benzyl compounds or reacting with carboalkoxy halide or benzoyl halide to give the (N-carboalkoxy or benzoyl-N-lower alkyl)-amino-N-benzylpiperidine or pyrrolidine and then removing the N-benzyl group by catalytic hydrogenation.

Alternatively, 1-(9-xanthenyl)piperidines and pyrrolidines of Formula I having an amino substituent in the 3-position of the piperidine or pyrrolidine ring are prepared by reacting a 9-aminoxanthene with an N-lower alkanoylaspartic anhydride or N-lower alkanoylglutamic anhydride, cyclizing the resulting amide by heating in acetic anhydride and reducing the resulting imide, for example using lithium aluminum hydride, to give 1-(9-xanthenyl)-3-lower alkylaminopiperidine or pyrrolidine. 1-(9-Xanthenyl)-3-ethylaminopyrrolidine was prepared by this procedure by Witiak et al., *J. Med. Chem.* 17:690–696 (1974).

The N,N-substituted aminomethyl, aminoethyl and aminopropyl piperidine and pyrrolidine starting materials (compounds of Formula IV in which $m$ is 1, 2 or 3) are either known to the art or are prepared by standard procedures, such as by reduction of the corresponding N,N-substituted aminomethyl, aminoethyl or aminopropyl pyridines and pyrroles, for example by hydrogenation with ruthenium dioxide or rhodium on carbon.

The pharmaceutically acceptable, acid addition salts of the compounds of Formula I (including the compounds of Formula II) are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric, and nitric acids. Of course these salts may also be prepared by the classical method of double decomposition of appropriate salts which is well-known to the art.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula I or a pharmaceutically acceptable acid addition salt thereof are objects of this invention.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula I or a pharmaceutically acceptable acid addition salt thereof. The active ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered one to four times per day. Dosage units will contain from about 10 mg. to about 500 mg., preferably from about 25 mg. to about 300 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The terms "lower alkyl" and "lower alkoxy" where used herein denote groups having, preferably, 1–4 carbon atoms; "lower alkanoyl" denotes groups having, preferably, 2–4 carbon atoms and "halogen" denotes chloro, bromo or fluoro.

The following examples are not limiting but are illustrative of the invention.

EXAMPLE 1

A suspension of 0.30 g. of platinum oxide in 20 ml. of absolute ethanol was shaken under 35 psi of hydrogen for 1 hour. To this was added a solution of 12.44 g. (65.9 mmoles) of 1-benzyl-3-piperidone and 4.1 g. (132 mmoles) of methylamine in 40 ml. of absolute ethanol. The mixture was then shaken under ca. 50 psi of hydrogen until uptake ceased. Filtration and evaporation afforded 1-benzyl-3-methylaminopiperidine.

A suspension of 0.30 g. of platinum oxide in 25 ml. of absolute ethanol was shaken under 35 psi of hydrogen for 1 hour. To this was added a solution of the 1-benzyl-3-methylaminopiperidine and 16 g. of 37 percent aqueous formaldehyde in 40 ml. of ethanol. The mixture was then shaken under ca. 50 psi of hydrogen until uptake ceased. Filtration and evaporation left an oil, which was dissolved in benzene and extracted with dilute hydrochloric acid. The extract was made strongly basic with sodium hydroxide and was extracted with methylene chloride. After drying, the solvent was evaporated, leaving 1-benzyl-3-dimethylaminopiperidine.

A mixture of 1-benzyl-3-dimethylaminopiperidine and 0.5 g. of 10 percent palladium on carbon in 100 ml. of methanol was heated to ca. 56°C. and shaken under ca. 40 psi of hydrogen until uptake ceased. The catalyst was filtered, and the solvent distilled at atmospheric pressure. Distillation of the residue afforded 3-dimethylaminopiperidine, b.p. 87°–89°C./28 mm.

Methyl isocyanate (20 g.) was added slowly, with stirring, to a filtered solution of 30 g. of xanthydrol in 100 ml. of anhydrous triethylamine. After standing for 40 minutes in a 20°C. water bath, the mixture was filtered. The collected solid was washed with anhydrous diethyl ether and dried in vacuo to give 9-(N-methylcarbamoyloxy)-xanthene.

To 15 g. of 9-(N-methylcarbamoyloxy)xanthene, suspended in 200 ml. of dry ether, was added 18 ml. of glacial acetic acid with stirring. After one hour, the lower acid layer was removed. The ether phase was then cooled, neutralized with cold aqueous sodium bicarbonate, dried over anhydrous magnesium sulfate and concentrated in vacuo. The residue was recrystallized from benzene-hexane to give 9-acetoxyxanthene, m.p. 109°–112°C.

A solution of 9.92 g. (41.3 mmoles) of 9-acetoxyxanthene and 5.9 g. (46.1 mmoles) of 3-dimethylaminopiperidine in 200 ml. of benzene was refluxed for 18 hours. The mixture was then washed with aqueous sodium bicarbonate solution, dried, and evaporated. Chromatography on alumina (chloroform eluant) afforded 1-(9-xanthenyl)-3-dimethylaminopiperidine, as a colorless oil.

EXAMPLE 2

A solution of 1-benzyl-4-piperidone in 40 ml. of absolute ethanol was added to a solution of 8.5 g. of methylamine in 40 ml. of ethanol. The resulting solution was added to a suspension of 0.5 g. of platinum oxide in 30 ml. of ethanol which had been pretreated with 50 psi of hydrogen for 1 hour. This suspension was reduced at 50 psi of hydrogen until one equivalent of hydrogen was consumed and then filtered. The filtrate was concentrated in vacuo to give 1-benzyl-4-methylaminopiperidine.

To a suspension of 0.5 g. of platinum oxide in 25 ml. of ethanol (prereduced as described above) was added a solution of the 1-benzyl-4-methylaminopiperidine and 29.7 ml. of 37 percent aqueous formaldehyde in 60 ml. of ethanol. This suspension was reduced at 50 psi of hydrogen until one equivalent of hydrogen was consumed. The mixture was then filtered and the filtrate concentrated in vacuo. A solution of the residue in benzene was extracted with dilute hydrochloric acid. The aqueous phase was made alkaline with 40 percent aqueous sodium hydroxide and extracted with methylene chloride. The organic layer was dried over anhydrous potassium carbonate and concentrated in vacuo to afford 1-benzyl-4-dimethylaminopiperidine.

A solution of the 1-benzyl-4-dimethylaminopiperidine in 125 ml. of methanol was shaken with 1.0 gm. of 10 percent palladium on carbon under 50 psi of hydrogen at 50°C. until one equivalent of hydrogen was consumed. The suspension was filtered and the filtrate concentrated at atmospheric pressure. The residue was distilled at 20 mm. Hg. to give 4-dimethylaminopiperidine, b.p. 90°–92°C.

A solution of 2.14 g. of 4-dimethylaminopiperidine and 4.0 g. of 9-acetoxyxanthene in 100 ml. of sieve dried benzene was refluxed for 24 hours. The mixture was then washed with a 5 percent aqueous solution of sodium carbonate, dried and the solvent removed in vacuo. The residue was recrystallized three times from hexane to afford 1-(9-xanthenyl)-4-dimethylaminopiperidine, m.p. 92°–93°C.

EXAMPLE 3

A solution of 3.12 g. (0.02 mole) of 2-(2-dimethylaminoethyl)piperidine and 4.8 g. (0.02 mole) of 9-acetoxyxanthene in 75 ml. of anhydrous benzene was refluxed for 20 hours. The cooled solution was washed with 100 ml. of a 5 percent aqueous sodium bicarbonate solution, dried over anhydrous potassium carbonate, filtered, and evaporated in vacuo. The residue was taken up in low boiling petroleum ether and filtered to remove dixanthenyl ether. The filtrate was chromatographed on 125 g. of alumina, eluting successively with petroleum ether, petroleum etherbenzene mixtures, benzene, and finally ether. Evaporation of the ether fractions gave 1-(9-xanthenyl)-2-(2-dimethylaminoethyl)piperidine, m.p. 64°–67°C.

EXAMPLE 4

A solution of 3.5 g. (14.6 mmoles) of 9-acetoxyxanthene and 2.1 g. (14.8 mmoles) of 2-(dimethylaminomethyl)-piperidine in 50 ml. of toluene was refluxed for 40 hours. The mixture was then washed with sodium bicarbonate, dried and evaporated. Recrystallization of the residue from hexane afforded 1-(9-xanthenyl)-2-(dimethylaminomethyl)-piperidine, m.p. 81°–83°C.

EXAMPLE 5

By the procedure of Example 1, hydrogenating 1-benzyl-3-piperidone and ethylamine, then treating the resulting 1-benzyl-3-ethylaminopiperidine with acetaldehyde and hydrogenating to give 1-benzyl-3-diethylaminopiperidine, and removing the benzyl group by hydrogenating with palladium on carbon in methanol gives 3-diethylaminopiperidine.

A solution of 9.92 g. of 9-acetoxyxanthene and 7.2 g. of 3-diethylaminopiperidine in 200 ml. of benzene is refluxed for 18 hours. Working up by the procedure of Example 1 gives 1-(9-xanthenyl)-3-diethylaminopiperidine.

Similarly, using propylamine and propionaldehyde in the above procedures, the product is 1-(9-xanthenyl)-3-dipropylaminopiperidine.

Also, using butylamine and butyraldehyde in the above procedures, 1-(9-xanthenyl)-3-dibutylaminopiperidine is obtained.

EXAMPLE 6

Using, in the procedure of Example 1, 3-diethylaminopyrrolidine in place of 3-dimethylaminopiperidine gives 1-(9-xanthenyl)-3-diethylaminopyrrolidine.

EXAMPLE 7

Using, in the procedure of Example 4, 2-(dimethylaminomethyl)pyrrolidine in place of 2-(dimethylaminomethyl)-piperidine gives 1-(9-xanthenyl)-2-(dimethylaminomethyl)-pyrrolidine.

EXAMPLE 8

By the procedure of Example 1, converting the following xanthydrols to the corresponding 9-acetoxyxanthenes and reacting with 3-dimethylaminopiperidine:
2-chloroxanthydrol
3-chloroxanthydrol
4-chloroxanthydrol
1-chloroxanthydrol
3-fluoroxanthydrol
2-bromoxanthydrol
the following products are obtained, respectively:
1-(2-chloro-9-xanthenyl)-3-dimethylaminopiperidine
1-(3-chloro-9-xanthenyl)-3-dimethylaminopiperidine
1-(4-chloro-9-xanthenyl)-3-dimethylaminopiperidine
1-(1-chloro-9-xanthenyl)-3-dimethylaminopiperidine
1-(3-fluoro-9-xanthenyl)-3-dimethylaminopiperidine
1-(2-bromo-9-xanthenyl)-3-dimethylaminopiperidine Reacting the substituted 9-acetoxyxanthenes with 3-diethylaminopyrrolidine gives the corresponding 1-(substituted-9-xanthenyl)-3-diethylaminopyrrolidines.

EXAMPLE 9

By the procedure of Example 1, converting the following xanthydrols to the corresponding 9-acetoxyxanthenes and reacting with 4-dimethylaminopiperidine by the procedure of Example 2:
3-methylxanthydrol
2-methylxanthydrol
2-ethylxanthydrol
2-t-butylxanthydrol
3-methoxyxanthydrol
2-ethoxyxanthydrol
2,7-dibromoxanthydrol
1,7-dimethoxyxanthydrol
1,8-dimethylxanthydrol
the following products are obtained, respectively:
1-(3-methyl-9-xanthenyl)-4-dimethylaminopiperidine
1-(2-methyl-9-xanthenyl)-4-dimethylaminopiperidine
1-(2-ethyl-9-xanthenyl)-4-dimethylaminopiperidine
1-(2-t-butyl-9-xanthenyl)-4-dimethylaminopiperidine
1-(3-methoxy-9-xanthenyl)-4-dimethylaminopiperidine
1-(2-ethoxy-9-xanthenyl)-4-dimethylaminopiperidine
1-(2,7-dibromo-9-xanthenyl)-4-dimethylaminopiperidine
1-(1,7-dimethoxy-9-xanthenyl)-4-dimethylaminopiperidine
1-(1,8-dimethyl-9-xanthenyl)-4-dimethylaminopiperidine.

EXAMPLE 10

A suspension of 25 g. of 3-chloro-6-methoxyxanthone in 175 ml. of 95 percent aqueous ethanol is poured into a flask containing sodium amalgam prepared from 9.0 g. of sodium and 55 ml. of mercury. The flask is stoppered and shaken vigorously for 20 minutes with intermittant venting. The amalgam is then allowed to settle and the ethanolic supernatant is decanted into 1.5 liters of water. The precipitate is filtered from the resulting mixture, washed with water, and air dried to yield 3-chloro-6-methoxyxanthydrol.

Using 3-chloro-6-methoxyxanthydrol in place of xanthydrol in the procedure of Example 1 gives 1-(3-chloro-6-methoxy-9-xanthenyl)-3-dimethylaminopiperidine.

Similarly, using the following xanthones as starting materials:
2-propylxanthone
3,6-dichloroxanthone
3-methoxy-6-methylxanthone
6-methoxy-2-methylxanthone
3-hydroxyxanthone
2-hydroxyxanthone
6-hydroxy-2-methylxanthone
the products are, respectively:

1-(2-propyl-9-xanthenyl)-3-dimethylaminopiperidine
1-(3,6-dichloro-9-xanthenyl)-3-dimethylaminopiperidine
1-(3-methoxy-6-methyl-9-xanthenyl)-3-dimethylaminopiperidine
1-(6-methoxy-2-methyl-9-xanthenyl)-3-dimethylaminopiperidine
1-(3-hydroxy-9-xanthenyl)-3-dimethylaminopiperidine
1-(2-hydroxy-9-xanthenyl)-3-dimethylaminopiperidine
1-(6-hydroxy-2-methyl-9-xanthenyl)-3-dimethylaminopiperidine.

EXAMPLE 11

A mixture of 10.2 g. of N-benzyl-3-methylaminopiperidine, prepared as in Example 1, and 5.05 g. of triethylamine in 150 ml. of dry chloroform was treated at 0°C. with a solution of 5.4 g. of carboethoxy chloride in 20 ml. of dry chloroform. After stirring for two hours, the mixture was poured into ice water and 5 percent aqueous sodium hydroxide added. The chloroform layer was separated, washed with water, and dried over potassium carbonate. The solvent was evaporated and the residue distilled in vacuo to give 1-benzyl-3-(N-carboethoxy-N-methyl)aminopiperidine.

The benzyl group is removed from the above prepared compound by catalytic hydrogenation according to the procedure of Example 1 to give 3-(N-carboethoxy-N-methyl)aminopiperidine.

Reaction of the above prepared 3-(N-carboethoxy-N-methyl)aminopiperidine with 9-acetoxyxanthene in benzene by the procedure of Example 1 gives 1-(9-xanthenyl)-3-(N-carboethoxy-N-methyl)aminopiperidine.

The above prepared 1-(9-xanthenyl)-3-(N-carbethoxy-N-methylamino)piperidine (4.5 g.) is refluxed with 100 ml. of a 5M solution of potassium hydroxide in 80 percent aqueous ethanol for three hours. The resulting solution is concentrated in vacuo and the residue poured into cold water. This mixture is extracted with methylene chloride and the organic phase is washed with water and dried over anhydrous potassium carbonate. Evaporation of the solvent gives 1-(9-xanthenyl)-3-methylaminopiperidine.

EXAMPLE 12

A mixture of 3.0 g. of 4-[2-(ethylamino)ethyl]-pyridine and 2.0 g. of triethylamine in 60 ml. of dry chloroform is treated at 0°C. with a solution of 2.1 g. of carboethoxy chloride in 10 ml. of dry chloroform. After stirring for two hours, the mixture is poured into ice water and 5 percent aqueous sodium hydroxide added. The chloroform layer is separated, washed with water and dried over potassium carbonate. The solvent is evaporated and the residue distilled in vacuo to give 4-[2-(N-carboethoxy-N-ethylamino)ethyl]pyridine.

A mixture of 5.0 g. of 4-[2-N-carboethoxy-N-ethylamino)ethyl]pyridine and 0.2 g. of ruthenium dioxide is hydrogenated at 100°C. and 80 atm. pressure until the uptake of hydrogen is complete. The product is dissolved in chloroform, filtered and the filtrate dried over potassium carbonate. The solvent is evaporated and the residue distilled in vacuo to give 4-[2-(N-carboethoxy-N-ethylamino)ethyl]piperidine.

Reaction of the above prepared 4-[2-(N-carboethoxy-N-ethylamino)ethyl]piperidine with 9-acetoxyxanthene in benzene by the procedure of Example 3 gives 1-(9-xanthenyl)-4-[2-(N-carboethoxy-N-ethylamino)ethyl]piperidine.

Treating the above prepared N-carboethoxy compound with potassium hydroxide in aqueous ethanol by the procedure of Example 11 gives 1-(9-xanthenyl)-4-[2-(ethylamino)ethyl]piperidine.

EXAMPLE 13

By the procedure of Example 12, using in place of the pyridine starting material, the following:
2-(methylamino)methylpyrrole
2-(ethylamino)methylpyrrole
the products obtained are, respectively:
1-(9-xanthenyl)-2-(methylamino)methylpyrrolidine
1-(9-xanthenyl)-2-(ethylamino)methylpyrolidine.

EXAMPLE 14

Using, in the procedure of Example 1, 1-benzyl-3-pyrrolidinone as a starting material in place of 1-benzyl-3-piperidone gives as the product 1-(9-xanthenyl)-3-dimethylaminopyrrolidine.

Using, in the procedure of Example 1, the substituted xanthydrols listed in Example 8 and 1-benzyl-3-pyrrolidinone the corresponding 1-(substituted 9-xanthenyl)-3-dimethylaminopyrrolidines are obtained.

EXAMPLE 15

A mixture of 1.0 g. of 1-(9-xanthenyl)-3-methylaminopiperidine and 2.0 g. of triethylamine in 25 ml. of dry chloroform is treated at 0°C. with 0.5 g. of acetic anhydride in 2 ml. of dry chloroform. The mixture is refluxed with stirring for two hours and then poured into ice water. The chloroform layer is washed with water, dried over potassium carbonate, and the solvent is removed in vacuo to give 1-(9-xanthenyl)-3-(N-acetyl-N-methylamino)-piperidine.

Similarly, using the following in place of acetyl anhydride:
propionyl anhydride
butyryl anhydride
the products are, respectively:
1-(9-xanthenyl)-3-(N-propionyl-N-methylamino)-piperidine
1-(9-xanthenyl)-3-(N-butyryl-N-methylamino)-piperidine.

Using 1-(9-xanthenyl)-4-[2-(ethylaminoethyl]-piperidine in place of 1-(9-xanthenyl)-3-methylaminopiperidine in the above procedure gives the following products:
1-(9-xanthenyl)-4-[2-(N-acetyl-N-ethylamino)-ethyl]piperidine
1-(9-xanthenyl)-4-[2-(N-propionyl-N-ethylamino)-ethyl]piperidine
1-(9-xanthenyl)-4-[2-(N-butyryl-N-ethylamino)-ethyl]piperidine.

By the same procedure, using 1-(9-xanthenyl)-2-(methylamino)methylpyrrolidine and 1-(9-xanthenyl)-2-(ethylamino)methylpyrrolidine, the corresponding N-acetyl, N-propionyl and N-butyryl compounds are prepared.

EXAMPLE 16

By the procedure of Example 1, reacting 9-acetoxyxanthene with 3-(3-dimethylaminopropyl)piperidine [prepared by hydrogenating 3-(3-dimethylaminopropyl)pyridine in the presence of ruthenium dioxide by the procedure of Example 12] gives 1-(9-xanthenyl)-3-[3-(dimethylamino)propyl]piperidine.

Similarly, the corresponding 2- and 4-[3-dimethylamino)propyl] compounds are prepared from 2-(3-dimethylaminopropyl)pyridine and 4-(3-dimethylaminopropyl)pyridine, respectively.

EXAMPLE 17

Reacting 1-(9-xanthenyl)-3-dimethylaminopiperidine with hydrogen chloride in ether at −10°C. gives the hydrochloride salt.

Also, reacting with concentrated sulfuric acid in ether gives 1-(9-xanthenyl)-3-dimethylaminopiperidine sulfate.

Reacting 1-(9-xanthenyl)-3-dimethylaminopiperidine in tetrahydrofuran and diethyl ether with an equivalent amount of dl-tartaric acid in tetrahydrofuran at 0°C. gives the tartrate salt of 1-(9-xanthenyl)-3-dimethylaminopiperidine.

EXAMPLE 18

| Ingredients | Amounts |
|---|---|
| 1-(9-Xanthenyl)-3-dimethylamino-piperidine | 200 mg. |
| Lactose | 75 mg. |
| Magnesium stearate | 5 mg. |

The ingredients are mixed and filled into a hard gelatin capsule.

EXAMPLE 19

| Ingredients | Amounts |
|---|---|
| 1-(9-Xanthenyl)-4-dimethylamino-piperidine | 150 mg. |
| Peanut oil | 100 mg. |

The ingredients are mixed and filled into a soft gelatin capsule.

EXAMPLE 20

| Ingredients | Amounts |
|---|---|
| 1-(9-Xanthenyl)-2-(2-dimethylamino-ethyl)piperidine | 100 mg. |
| Lactose | 75 mg. |

The ingredients are mixed and filled into a hard gelatin capsule.

EXAMPLE 21

| Ingredients | Amounts |
|---|---|
| 1-(9-Xanthenyl)-3-dimethylamino-piperidine | 100 mg. |
| Polyethylene glycol | 2 ml. |

The above ingredients are used to prepare a solution for parenteral administration.

What is claimed is:

1. A pharmaceutical composition having gastric acid secretion inhibitory activity, in dosage unit form, comprising a pharmaceutical carrier in a xanthenyl compound of the formula:

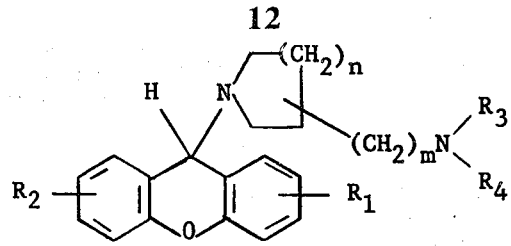

in which:
n is 1 or 2;
m is 0, 1, 2 or 3;
$R_1$ is hydrogen, halogen, hydroxy, lower alkyl or lower alkoxy;
$R_2$ is hydrogen, halogen, lower alkyl or lower alkoxy;
$R_3$ is lower alkyl;
$R_4$ is hydrogen, lower alkyl or lower alkanoyl or a pharmaceutically acceptable acid addition salt thereof, with the proviso that when m is 0, the amino group is not attached at the 2-position.

2. A pharmaceutical composition of claim 1 in which $R_1$ and $R_2$, being the same or different, are hydrogen, chloro, methyl or methoxy.

3. A pharmaceutical composition of claim 1 in which n is 2, $R_1$ and $R_2$ are hydrogen and $R_4$ is lower alkyl.

4. A pharmaceutical composition of claim 1 in which the xanthenyl compound is 1-(9-xanthenyl)-3-dimethylaminopiperidine.

5. A pharmaceutical composition of claim 1 in which the xanthenyl compound is 1-(9-xanthenyl)-4-dimethylaminopiperidine.

6. A pharmaceutical composition of claim 1 in which the xanthenyl compound is 1-(9-xanthenyl)-2-(2-dimethylaminoethyl)piperidine.

7. A pharmaceutical composition of claim 1 in which the xanthenyl compound is 1-(9-xanthenyl)-2-(dimethylaminomethyl)piperidine.

8. A pharmaceutical composition of claim 1 in which the xanthenyl compound is present in an amount of from about 10 mg. to about 500 mg.

9. A method of inhibiting gastric acid secretion comprising administering to an animal a xanthenyl compound of the formula:

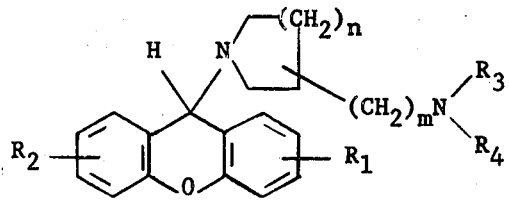

in which:
n is 1 or 2;
m is 0, 1, 2 or 3;
$R_1$ is hydrogen, halogen, hydroxy, lower alkyl or lower alkoxy;
$R_2$ is hydrogen, halogen, lower alkyl or lower alkoxy;
$R_3$ is lower alkyl;
$R_4$ is hydrogen, lower alkyl or lower alkanoyl or a pharmaceutically acceptable acid addition salt thereof, with the proviso that when m is 0, the amino group is not attached at the 2-position.

10. A method of claim 9 in which n is 2; $R_1$ and $R_2$ are hydrogen and $R_3$ and $R_4$ are lower alkyl.

11. A method of claim 9 in which the xanthenyl compound is 1-(9-xanthenyl)-3-dimethylaminopiperidine.

12. A method of claim 9 in which the xanthenyl compound is administered in a daily dosage of from about 10 mg. to about 2 g.

13. A compound of the formula:

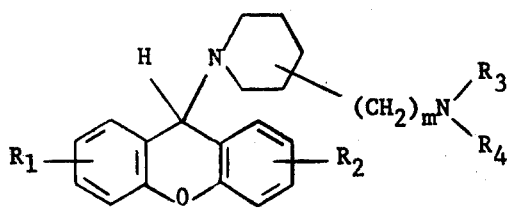

in which:

$m$ is 0, 1, 2 or 3;

$R_1$ is hydrogen, halogen, hydroxy, lower alkyl or lower alkoxy;

$R_2$ is hydrogen, halogen, lower alkyl or lower alkoxy;

$R_3$ is lower alkyl;

$R_4$ is hydrogen, lower alkyl or lower alkanoyl or a pharmaceutically acceptable acid addition salt thereof, with the proviso that when $m$ is 0, the amino group is not attached at the 2-position.

14. A compound of claim 13 in which $R_4$ is lower alkyl.

15. A compound of claim 13 in which $R_1$ and $R_2$, being the same or different, are hydrogen, chloro, methyl or methoxy.

16. A compound of claim 13 in which $R_1$ and $R_2$ are hydrogen and $R_4$ is lower alkyl.

17. A compound of claim 13 said compound being 1-(9-xanthenyl)-3-dimethylaminopiperidine.

18. A compound of claim 13 said compound being 1-(9-xanthenyl)-4-dimethylaminopiperidine.

19. A compound of claim 13 said compound being 1-(9-xanthenyl)-2-(2-dimethylaminoethyl)piperidine.

20. A compound of claim 13 said compound being 1-(9-xanthenyl)-2-(dimethylaminomethyl)piperidine.

* * * * *

UNITED STATES PATENT AND TRADEMARK OFFICE
CERTIFICATE OF CORRECTION

PATENT NO. : 3,980,788
DATED : September 14, 1976
INVENTOR(S) : Paul E. Bender and Bernard Loev It is certified that error appears in the above—identified patent and that said Letters Patent are hereby corrected as shown below:

Column 3, line 38, "M is O" should read -- m is O -- .

Column 11, line 65, after carrier , "in" should read -- and -- .

Signed and Sealed this

Twenty-eighth Day of December 1976

[SEAL]

Attest:

RUTH C. MASON
Attesting Officer

C. MARSHALL DANN
Commissioner of Patents and Trademarks